United States Patent [19]

Nagasawa et al.

[11] 4,094,897
[45] June 13, 1978

[54] RESIN-BONDED GRAPHITE BODY FOR A DRY CELL

[75] Inventors: Masahiro Nagasawa; Tomio Ishida, both of Hirakata; Yoshitaka Yoshikawa, Neyagawa, all of Japan

[73] Assignee: Matsushita Electric Industrial Co., Ltd., Japan

[21] Appl. No.: 711,377

[22] Filed: Aug. 3, 1976

[30] Foreign Application Priority Data

Aug. 12, 1975   Japan .................................. 50/98207

[51] Int. Cl.² .............................................. B32B 19/00
[52] U.S. Cl. .................................... 264/105; 264/294; 264/320; 264/325; 423/448
[58] Field of Search ...................... 264/294, 29.1, 320, 264/325, 296, 63, 104–105, 108, 236; 423/448; 429/209

[56] References Cited

U.S. PATENT DOCUMENTS

| | | | |
|---|---|---|---|
| 630,397 | 8/1899 | Niedringhaus | 264/294 |
| 1,417,743 | 5/1922 | Kempton | 264/294 |
| 3,008,744 | 11/1961 | Thomas | 264/294 |
| 3,168,509 | 2/1965 | Juel | 264/105 |
| 3,197,527 | 7/1965 | Krummeich | 264/105 |
| 3,255,277 | 6/1966 | Smith | 264/294 |
| 3,346,678 | 10/1967 | Ohlgren | 264/29.1 |
| 3,405,012 | 10/1968 | Balaguer | 264/29.1 |
| 3,438,848 | 4/1969 | Greiner | 264/294 |
| 3,634,569 | 1/1972 | Emanuelson et al. | 264/105 |

*Primary Examiner*—Jeffery R. Thurlow
*Attorney, Agent, or Firm*—Wenderoth, Lind & Ponack

[57] ABSTRACT

A resin-bonded graphite body having controlled crystalline orientation and a density of at least 2.05 g/cm³, the body comprising 3 to 12 weight % of a thermosetting resin and 88 to 97 weight % of a carbonaceous powder which includes at least 50 weight % of natural crystalline graphite powder, is provided. The body has a high transverse strength and a very low electrical resistance in the direction parallel to the direction of the crystalline orientation, and is thus suitable for a dry battery electrode.

11 Claims, 2 Drawing Figures (A)

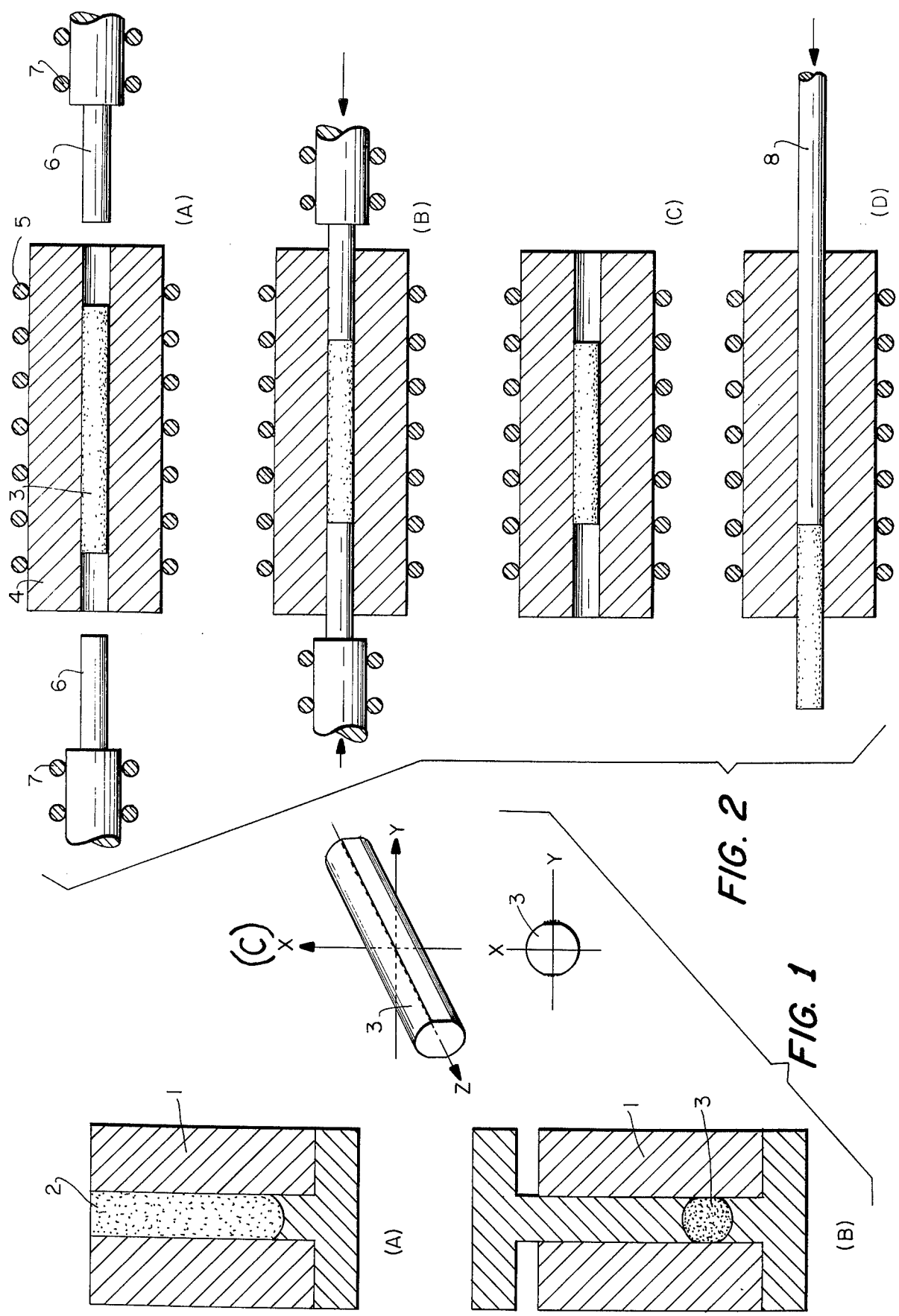

RESIN-BONDED GRAPHITE BODY FOR A DRY CELL

This invention relates to a resin-bonded graphite body for a dry battery and to a method of making the same.

According to a usual method of making a carbon (or graphite) electrode for a dry battery, a powder mixture of natural graphite, artificial graphite, cokes, soot (such as carbon black and acetylene black), etc. in a suitable mixture ratio is first prepared. Pitch and/or tar is added to the powder mixture into a uniform blend. The blend is formed into a rod shape by being heated and extruded through an outlet opening of an extruding machine which opening defines the cross-section of the resultant rod. The thus made rod is fired at 900° to 1000° C in a non-oxidizing atmosphere so as to carbonize the pitch and tar in the rod. The rod is then subjected to a waterproofing treatment by impregnating a wax such as paraffin into cracks and open pores in the rod produced during the firing (so-called wax impregnation).

Such conventional method has several disadvantages. Firstly, pitch and tar necessarily used therein are noxious materials containing materials which are likely to cause cancer. Secondly, the firing process causes a large amount of gas including organic gases to exhaust, resulting in air pollution. Thirdly, for preventing growth of cracks in the bodies, the bodies are gradually heated to the firing temperature and are also gradually cooled to room temperature after the firing. This expends a long time, e.g. 5 to 10 days, for the firing process. Fourthly, since fine cracks and open pores are unavoidably produced in the treated bodies due to the carbonization of pitch and tar, the bodies are required to be subjected to the troublesome water-proof treatment, because electrodes for dry batteries need water-proofing.

It is known that so-called resin-bonded (unsintered) graphite bodies can be prepared without the need for the above-described method which causes the above-described disadvantages. Resin-bonded graphite bodies are usually made by mixing an artificial graphite powder and a thermosetting resin such as phenolic resin, and molding the mixture. This kind of technique is taught e.g. by U.S. Pat. Nos. 3,405,012 and 3,634,569.

It is known that the mechanical strength of a resin-bonded graphite body increases as the amount of resin, as a binder, increases, and that the electrical (and thermal) conductivity of the body very much decreases as the amount of resin increases. Further, it is known that the mechanical strength and the electrical conductivity of the body increase as the density of the body increases. However, according to conventional techniques, which use the usual molding technique, it is very difficult to obtain a body having a density of not less than 2.0 g/cm$^3$ (and thus conventional resin-bonded graphite bodies most likely have densities less than 2.0 g/cm$^3$). Therefore, it has been very difficult to obtain both the mechanical strength and the conductivity of the resin-bonded graphite body which are comparable to those of the fired carbon or graphite body. This is why a resin-bonded graphite body has not been used for a dry battery electrode where the electrode is required to have both a very high mechanical strength (e.g. at least 300 kg/cm$^2$ or 500 kg/cm$^2$ in terms of transverse srrength) and a very high electrical conductivity (e.g. not more than $5 \times 10^{-3}$ Ω·cm or $4 \times 10^{-3}$ Ω·cm in terms of specific resistivity).

An object of this invention is to provide a resin-bonded graphite body and a method of making a resin-bonded graphite body having both a high mechanical strength and a high electrical conductivity.

This object of this invention is achieved by a resin-bonded graphite body having controlled crystalline orientation and a density of at least 2.05 g/cm$^3$, the body comprising 3 to 12 weight % of a thermosetting resin and 88 to 97 weight % of a carbonaceous powder which includes at least 50 weight % of natural crystalline graphite powder, wherein such resin-bonded graphite body can be made by: uniformly mixing, into a dry powdered mixture, 3 to 12 weight % of a thermosetting resin and 88 to 97 weight % of a carbonaceous powder which includes at least 50 weight % of natural crystalline graphite; compressing the dry mixture by a first uniaxial pressure into a compressed powder rod having crystalline orientation; inserting the compressed powder rod in a hollow of a mold which hollow has a shape similar to the shape of the compressed powder rod and defines resultant graphite body shape with the crystalline orientation being kept; pre-heating the thus inserted powder rod to the softening temperature of the thermosetting resin; compressing the thus pre-heated rod by a second uniaxial pressure, the direction of which is perpendicular to the direction of the first uniaxial pressure, and heating the rod to a curing temperature of the thermosetting resin so as to harden the thermosetting resin; and taking the thus treated rod out of the mold.

Details of this invention will be described hereinafter with reference to the accompanying drawings, in which:

FIG. 1 (A), 1 (B) and 1 (C) are schematic views of a powder, a mold and a compressed powder rod typically employed in the method of making a resin-bonded graphite body according to this invention; and FIGS. 2 (A), 2 (B), 2 (C) and 2 (D) are schematic views of a compressed powder rod, a mold and a final graphite body from one typical step of compressing and heating the compressed powder rod.

A carbon or graphite body for a dry battery electrode is desired to have electrical conductivity, a high mechanical strength and a high chemical stability, and is most desirably highly waterproof.

Since it is necessary to make the inner electrical resistance of a dry battery low, an electrode for the dry battery is usually desired to be less than $5 \times 10^{-3}$ Ω·cm, more preferably less than $4 \times 10^{-3}$ Ω·cm. Further, for preventing the electrode from being broken during the battery manufacturing process, the electrode is desired to have a transverse strength of at least 300 kg/cm$^2$, more preferably at least 500 kg/cm$^2$. Further, the electrode is required to be chemically stable so that it does not react with an electrolyte which is used in the battery, because otherwise the performance of the battery deteriorates. In addition, for preventing the electrolyte from leaking out of the battery through the electrode, the electrode is required to be of liquid-proof.

It has been found according to this invention that the above requirements can be met by a resin-bonded graphite body having controlled crystalline orientation and a density of at least 2.05 g/cm$^3$, the body comprising 3 to 12 weight % of a thermosetting resin and 88 to 97 weight % of a carbonaceous powder which includes at least 50 weight % of natural crystalline graphite powder. The word "graphite body having controlled crystalline orientation" used herein means a body in which the basal plane of each crystalline graphite particle is substantially parallel to the same plane.

The carbonaceous powder used in this invention is required to include natural crystalline graphite as a main component. The "natural crystalline graphite" is a generic name representing natural graphite such as those usually referred to as flake graphite and plumbago, the particles of which are well grown crystallites. For reducing the cost of the resultant graphite body of this invention, conductive carbonaceous powders other than the natural crystalline graphite, such as natural amorphous graphite, artificial graphite, cokes and soots, can also be used. However, in such case also, the carbonaceous powder used in this invention should include at least 50 weight % of natural crystalline graphite. Best results can be obtained when the carbonaceous powder is composed of 100 weight % of natural crystalline graphite, and the electrical conductivity and/or mechanical strength of the resultant graphite body decrease as the amount of the other carbonaceous powders increases. In the case of natural amorphous graphite and artificial graphite, they can substitute natural crystalline graphite in an amount of up to 50 weight % of the whole carbonaceous powder, because the degree of deterioration of the performance of the resultant graphite body due to the substitution is relatively low. On the other hand, in the case of cokes and soot, although they can also substitute natural crystalline graphite, the amount of the substitution should be less than 20 weight % of the carbonaceous powder, because the degree of deterioration of the performance of the resultant graphite body is high.

The particle size of natural crystalline graphite affects the electrical conductivity and the mechanical strength of the resultant graphite body. Better results can be obtained in this respect when the average particle size of natural crystalline graphite is between 50 microns and 150 microns.

The binder used in this invention should be a thermosetting resin. Phenolic resin, epoxy resin, xylic resin, urea-formaldehyde-resin, etc. can be used therefor. Among them, the best one is epoxy resin in view of the electrical conductivity, mechanical strength and chemical stability of the resultant graphite body. Xylic resin can also be recommended because it provides resultant properties comparable to those provided by epoxy resin and is less expensive than epoxy resin. The amount of the thermosetting resin in the graphite body is desired to be between 3 and 12 weight %. If it is less than 3 weight %, the resultant mechanical strength becomes undesirably low, whereas if it is more than 12 weight %, the resultant electrical conductivity becomes undesirably low.

The density of the graphite body comprised of one of the preferred compositions as set forth above, depends on the method of making the graphite body from the composition. It has been found according to this invention that a very high density can be obtained by using a new method, and that when the density is at least 2.05 g/cm$^3$, excellent electrical conductivity and mechanical strength can be obtained, whereas when the density is less than 2.05 g/cm$^3$, satisfactory results cannot be obtained.

Hereinafter, the method of making a graphite body according to this invention will be described.

As a first step, a powder mixture is prepared by uniformly mixing 3 to 12 weight % of a thermosetting resin and 88 to 97 weight % of a carbonaceous powder which includes at least 50 weight % of natural crystalline graphite. It is preferred that unnecessary liquid materials not be contained in the powder mixture, so as to make the powder mixture as dry as possible. If a viscous resin is used as a thermosetting resin, the resin is preferred to be dissolved in a solvent so as to increase the uniformity of the powder mixture. However, in such case also, it is desired to make the powder mixture dry by evaporating the solvent off after the mixing step. An effective method for obtaining a dry powder mixture is to use, as the binder, a fine powdered resin in a dry state. Thereby, an excellent powder mixture, which has a volume density of not more than 0.5 g/cm$^3$, can be obtained.

As a next step, the powder mixture is compressed by a uniaxial pressure into a compressed powder in the form of a rod similar to the desired rod shape of an electrode for a dry battery. (This uniaxial pressure can be called a first uniaxial pressure in view of a uniaxial pressure used at a later stage which can be called second uniaxial pressure.) The direction of uniaxial pressure is preferred to be perpendicular to the direction of the length of the resultant compressed powder rod. This step can more readily understood with reference to FIG. 1 (A), FIGS. 1 (B) and FIG. 1 (C).

FIG. 1 (A) shows a schematic cross-sectional view of a mold in which a powder mixture is charged before the compression step. Reference numeral 1 designates a mold for compression, and reference numeral 2 designates a powder mixture charged in the hollow of the mold 1. FIG. 1 (B) shows a schematic cross-sectional view of the mold, after the compression step, in which a compressed powder rod is made. Reference numeral 3 designates a compressed powder rod. FIG. 1 (C) is a schematic perspective view together with a schematic cross-sectional view of the compressed powder rod 3. With reference to FIG. 1 (C), the direction of the length of the compressed powder rod 3 and the direction of the uniaxial pressure are defined as $z$ direction and $x$ direction, respectively, and the direction perpendicular to both the $z$ and $x$ directions is defined as $y$ direction, for the sake of easy explanation.

Since the electrode in a dry battery usually has a form of a rod having a cross-section of circle, the compressed powder rod 3 is also preferred to have a circle-like cross-section as shown in FIG. 1 (C). The uniaxial pressure for the compression step is preferred to be between about 150 and about 800 kg/cm$^2$. When the pressure is less than 150 kg/cm$^2$, the mechanical strength of the resultant compressed powder rod is likely to be insufficient for easily treatment of the powder rod in subsequent steps. On the other hand, when the pressure is more than 800 kg/cm$^2$, cracks are likely to occur in the rod in the subsequent heating and further compressing step.

The compressed powder rod made by the compression step (by the first uniaxial pressure) has a controlled crystalline orientation. That is, the basal plane (the plane perpendicular to the c-axis of the crystallite) of each crystalline graphite particle in the compressed powder rod is substantially parallel to one plane ($y$-$z$ plane). When the amount of natural crystalline graphite in the carbonaceous powder is less than 50 weight %, and/or when the powder mixture is in a wet state, and/or when the volume density of the powder mixture is unnecessarily high, then sufficient crystalline orientation cannot be obtained, and the electrical conductivity and the mechanical strength of the resultant graphite body (electrode) are likely to be insufficient. Further, the compressed powder rod is preferred to have an apparent density between 1.6 and 1.8 g/cm$^3$. When the density is less than 1.6, sufficient crystalline orientation and mechanical strength are difficult to obtain, whereas when the density is higher than 1.8, gases in the rod do not easily escape from the rod during the heating, and cracks are likely to occur in the rod.

As a next step, the compressed powder rod is further compressed by a uniaxial pressure (second uniaxial pressure) and is heated to cure the thermosetting resin in the powder rod so as to obtain a final graphite body (electrode for a dry battery). This step will be described below with reference to FIGS. 2 (A), 2 (B), 2 (C) and 2 (D).

Referring to FIGS. 2 (A) to 2 (D), reference numeral 4 designates a mold having a heater 5 attached thereto. Reference numeral 6 designates a press piston having a heater 7 attached thereto. FIG. 2 (A) shows the state where the compressed powder rod 3 is inserted in a hollow of the mold. It is preferred that the cross-section of the hollow has a shape similar to and slightly larger than the shape of the cross-section of the powder rod 3. The powder rod 3 is placed in the mold 4 so that a uniaxial pressure (second uniaxial pressure) the direction of which is perpendicular to the x direction can be applied to the powder rod 3. That is, a uniaxial pressure the direction of which is parallel to the basal plane of the crystallites, i.e. z direction.

After the powder rod 3 is inserted in the mold 4. the mold 4 and the powder rod 3 are heated by the heater 5 to the softening temperature of the thermosetting resin in the powder rod 3. (This is a pre-heating step in view of the subsequent heating step to cure the resin.) This pre-heating step also functions to get rid of the gas contained in the powder rod 3. Then, a uniaxial pressure is applied to the powder rod 3 in the z direction by using the press piston 6 as shown in FIG. 2 (B). Thereby, the powder rod 3 is compressed in the z direction.

The powder rod 3 is also heated to the curing temperature of the thermosetting resin in the powder rod 3 by using the heaters 5 and 7 so as to harden the resin. Thereafter, the piston 6 is taken out as shown in FIG. 2 (C), and the rod which is now a resin-bonded graphite body is taken out of the mold 4 by using a knockout piston 8 as shown in FIG. 2 (D). One preferable manner of carrying out the compressing step as shown in FIG. 2 (A) to FIG. 2 (D) is: to pre-heat the mold 4 and the piston 6 to a temperature not lower than the curing temperature of the thermosetting resin by using the heaters 5 and 7; and then to insert the powder rod 3 into the mold 4; and to maintain the rod 3 as is, until the thermosetting resin in the rod 3 is heated to about the softening temperature thereof by the heat from the preheated mold 4; and then to insert the piston 6 into the mold so as to compress the rod in the z direction; and to maintain the pressure for a suitable time to cure the thermosetting resin.

The relation between the cross-sectional area of the powder rod 3 (cut by the xy plane) and the cross-sectional area of the hollow of the mold 4 or the cross-sectional area of the piston 6 (cut also by the xy plane) is as follows. The latter cross-sectional area is preferred to be between 1.02 and 1.16 times as large as the former cross-sectional area. When it is less than 1.02, it becomes rather difficult to insert the powder rod in a mold such as the mold 4 as shown, while when it is more than 1.16, the desired crystalline orientation in the rod is likely to be damaged by the second compression step (in the z direction), resulting in difficulty in obtaining a graphite body of high density, high mechanical strength and high electrical conductivity.

Suitable temperatures for heating the mold 4 and the piston 6 depend on the kind of the employed thermosetting resin, but are usually preferred to be between 150° and 200° C. The (second) uniaxial pressure for the (second) compression is preferred to be between 500 and 2,000 kg/cm$^2$. Broadly speaking, better results can be obtained as the pressure increases, but when it is more than 2000 kg/cm$^2$, the increment of the pressure from 2000 kg/cm$^2$ does not substantially give a noticeable improvement, so that it is substantially useless to increase the pressure over 2000 kg/cm$^2$.

One of the most important aspects of this invention is that a well crystalline oriented powder body (rod) be made by the powder compression step (first compression step), and the powder body be subjected to the second compression step in the direction parallel to the basal plane of the oriented crystallites, and be heated to cure the thermosetting resin. By the method of making a graphite body according to this invention as described above, the orientation of the crystallites formed by the first compression step is substantially maintained after the second compression step. And it is presumed that many crystallites, which are parallel to the yz plane after the first compression, are made to slide into gaps between adjacent crystallites, resulting in the obtention of a resin-bonded graphite body of a high density.

The crystalline orientation can be examined by the well known X-ray analysis, but it is more convenient to examine the crystalline orientation by observing coloration of crystallites under the crossed nicols (polarizer and analyzer) of a polarizing microscope. When the c-axis of the crystallites coincide with the polarization direction of the analyzer, the crystallites are observed to be blue, while when the c-axis is perpendicular to the polarization direction, the crystallites are observed to be gold yellow. The crystalline orientation in a certain direction can be measured by: cutting the graphite body by a plane parallel to the certain direction; polishing the cut surface to a mirror surface; making the polarization direction of the analyzer coincide with the specific direction of the orientation to be measured; measuring the ratio of the blue colored area to the whole area subjected to the measurement; and carrying out the same measurement after rotating the angle of the sample or the analyzer by 90°, thereby to measure the ratio of the blue colored area to the whole area subjected to the measurement. The ratio between the thus measured two ratios represents the degree of orientation of the crystallites in the above-mentioned certain direction.

When measured by such methods, the crystalline orientation (strictly speaking, the orientation of the c-axis of the crystallites in the x direction) of the body according to the graphite body provided by this invention is found to be mostly at least 90 %, and to be at least 95 % in the case of more preferred embodiments.

The following EXAMPLES are meant to illustrate preferred embodiments of this invention, some in comparison with non-preferred samples, but are not meant to limit the scope thereof.

EXAMPLE 1

Sixteen powder mixtures each composed of natural crystalline graphite powder having an average particle size of 75 microns and finely powdered xylic resin as a thermosetting resin in an amount listed in Table I were prepared. The volume densities of these mixtures more or less depended on the amount of the used xylic resin, but fell within the range between 0.30 and 0.33 g/cm³. Each powder mixture was charged in a mold as shown in FIG. 1 (A) in a natural heap state, and was then compressed by a pressure of about 200 kg/cm² in the $x$ direction as shown in FIG. 1 (B) and FIG. 1 (C) into a powder rod (preform) as shown by reference numeral 3 in FIG. 1 (C). The rod had a length (in the $z$ direction) of 76 mm, a height (in the $x$ direction) of 8.0 mm and a width (in the $y$ direction) of 7.6 mm.

Besides, a mold having a cylindrical hollow as shown in FIG. 2 (A) was preliminarily heated to 200° C. The above prepared rod (preform) was inserted in the thus prepared mold and was kept there for about 20 seconds so as to soften the xylic resin. Then, a piston means heated to 200° C as shown by reference numeral 6 in FIG. 2 (A) was inserted in the mold so as to apply a pressure of 500 kg/cm² to the rod in the $z$ direction thereof, and the pressure was maintained for 90 seconds so as to cure the xylic resin.

Then, the thus compressed rod (resin-bonded graphite body) was taken out of the mold. The thus made rod was measured as to its density, specific resistivity in the $z$ direction, and transverse strength. Table I lists the results of the measurements.

EXAMPLE 2

92 weight % of natural crystalline graphite having an average particle size of 50 microns and 8 weight % of finely powdered xylic resin were blended and well mixed by a powder mixer to make a powder mixture having a volume density of 0.32g/cm³. By using this powder mixture, a resin-bonded graphite body (Sample 17) was prepared in a manner similar to that used in EXAMPLE 1.

For comparison, Samples 18 and 19 were prepared by using the same powder mixture as above used for making Sample 17, except that in the case of Sample 18, the powder rod (preform) was made by compressing the powder heap in the $z$ direction instead of the $x$ direction, and the second compression (in the resin-curing mold) was also carried out in the same $z$ direction, while in the case of Sample 19, the powder heap was directly compressed by the resin-curing mold without being first formed to a powder rod (preform).

These three Samples were measured as to the density, resistivity and transverse strength. Table II lists the results of the measurements.

EXAMPLE 3

Eight graphite (carbonaceous) powders each composed of natural crystalline graphite powder and natural amorphous graphite powder in amounts as listed in Table III were prepared. 94 weight % of each of the thus prepared graphite (carbonaceous) powders and 6 weight % of finely powdered xylic resin were well mixed. Thereby, eight powder mixture were prepared. By using these powder mixtures, eight resin-bonded graphite bodies were made in a manner the same as that done in EXAMPLE 1. The thus made graphite bodies were measured as to the density, resistivity and transverse strength. Table III lists the results of the measurements.

EXAMPLE 4

92 weight % of natural crystalline graphite powder having an average particle size of 150 microns and 8 weight % of a viscous epoxy resin including a hardener (curing agent) were blended. Methylethylketone as a solvent was added to the blend, and the thus made blend was well wet-milled by using a ball mill. The thus made mixture was separated into five portions. These five portions were dried under five drying conditions, respectively, so as to obtain five powder mixtures having the same composition but different volume densities as listed in Table IV.

From the thus made five powder mixtures, five graphite bodies were made, respectively, in a manner the same as that in EXAMPLE 1. These graphite bodies were measured as the density, resistivity and transverse strength. Table IV lists the results of the measurements.

Table I

| Sample No. | Resin content (wt. %) | Density (g/cm³) | Resistivity (ohm-cm) | Transverse strength (kg/cm²) |
|---|---|---|---|---|
| 1 | 0 | 2.09 | $1.3 \times 10^{-3}$ | 40 |
| 2 | 1 | 2.14 | $1.3 \times 10^{-3}$ | 80 |
| 3 | 2 | 2.17 | $1.4 \times 10^{-3}$ | 180 |
| 4 | 3 | 2.20 | $1.6 \times 10^{-3}$ | 300 |
| 5 | 4 | 2.20 | $1.8 \times 10^{-3}$ | 380 |
| 6 | 5 | 2.19 | $2.1 \times 10^{-3}$ | 450 |
| 7 | 6 | 2.17 | $2.3 \times 10^{-3}$ | 500 |
| 8 | 7 | 2.15 | $2.5 \times 10^{-3}$ | 570 |
| 9 | 8 | 2.13 | $2.9 \times 10^{-3}$ | 600 |
| 10 | 9 | 2.11 | $3.3 \times 10^{-3}$ | 630 |
| 11 | 10 | 2.09 | $3.7 \times 10^{-3}$ | 640 |
| 12 | 12 | 2.05 | $5.0 \times 10^{-3}$ | 650 |
| 13 | 14 | 2.01 | $6.8 \times 10^{-3}$ | 660 |
| 14 | 16 | 1.97 | $9.3 \times 10^{-3}$ | 650 |
| 15 | 18 | 1.94 | $13 \times 10^{-3}$ | 630 |
| 16 | 20 | 1.90 | $19 \times 10^{-3}$ | 600 |

Table II

| Sample No. | Density (g/cm³) | Resistivity (ohm-cm) | Transverse strength (kg/cm²) |
|---|---|---|---|
| 17 | 2.13 | $2.9 \times 10^{-3}$ | 600 |
| 18 | 2.03 | $21 \times 10^{-3}$ | 250 |
| 19 | 1.95 | $24 \times 10^{-3}$ | 180 |

Table III

| Sample No. | Composition of graphite powder crystalline (wt. %) | Composition of graphite powder amorphous (wt. %) | Density (g/cm³) | Resistivity (ohm-cm) | Transverse strength (kg/cm²) |
|---|---|---|---|---|---|
| 20 | 100 | 0 | 2.17 | $2.7 \times 10^{-3}$ | 550 |
| 21 | 90 | 10 | 2.15 | $2.7 \times 10^{-3}$ | 530 |
| 22 | 80 | 20 | 2.13 | $2.9 \times 10^{-3}$ | 500 |
| 23 | 70 | 30 | 2.11 | $3.5 \times 10^{-3}$ | 470 |
| 24 | 60 | 40 | 2.09 | $4.2 \times 10^{-3}$ | 440 |
| 25 | 50 | 50 | 2.07 | $4.8 \times 10^{-3}$ | 400 |
| 26 | 40 | 60 | 2.04 | $6.5 \times 10^{-3}$ | 330 |
| 27 | 30 | 70 | 2.00 | $9.0 \times 10^{-3}$ | 280 |

Table IV

| Sample No. | Volume density of mixed powder (g/cm³) | Density (g/cm³) | Resistivity (ohm-cm) | Transverse strength (kg/cm²) |
|---|---|---|---|---|
| 28 | 0.35 | 2.15 | $2.7 \times 10^{-3}$ | 620 |
| 29 | 0.38 | 2.13 | $2.9 \times 10^{-3}$ | 610 |
| 30 | 0.45 | 2.10 | $3.4 \times 10^{-3}$ | 520 |
| 31 | 0.50 | 2.05 | $4.5 \times 10^{-3}$ | 400 |
| 32 | 0.60 | 1.98 | $5.8 \times 10^{-3}$ | 320 |

What is claimed is:

1. A method of making a resin-bonded graphite body, comprising:

uniformly mixing, to form a dry powder mixture, 3 to 12 weight % of a thermosetting resin and 88 to 97 weight % of a carbonaceous powder which includes at least 50 weight % of natural crystalline graphite particles, compressing said dry mixture by a first uniaxial pressure into a compressed powder rod having crystalline orientation;

inserting said compressed powder rod into a hollow of a mold which has a shape similar to the shape of said compressed powder rod;

pre-heating the thus inserted powder rod to the softening temperature of said thermosetting resin;

compressing the thus pre-heated rod by a second uniaxial pressure, the direction of which is perpendicular to the direction of said first uniaxial pressure and parallel to the direction of the length of said powder rod as well as to the basal plane of said crystalline graphite particles;

heating said rod to the curing temperature of said thermosetting resin so as to harden said thermosetting resin, said orientation being maintained after said curing; and removing the thus treated rod from said mold.

2. A method according to claim 1, wherein said natural crystalline graphite has an average particle size of 50 to 150 microns.

3. A method according to claim 1, wherein said thermosetting resin is epoxy resin.

4. A method according to claim 1, wherein said thermosetting resin is xylic resin.

5. A method according to claim 1, wherein said thermosetting resin is a fine powder.

6. A method according to claim 1, wherein said powder mixture has a volume density of not more than 0.5 g/cm$^3$.

7. A method according to claim 1, wherein said first uniaxial pressure is 150 to 800 kg/cm$^2$.

8. A method according to claim 1, wherein said compressed powder rod has an apparent density between 1.6 and 1.8 g/cm$^3$.

9. A method according to claim 1, wherein the cross-sectional area of said hollow of said mold is between 1.02 and 1.16 times as large as the cross-sectional area of said powder rod.

10. A method according to claim 1, wherein said second uniaxial pressure is 500 to 2,000 kg/cm$^2$.

11. A method according to claim 1, wherein said pre-heating step and the subsequent compressing step are carried out by: pre-heating said mold and piston for said compression to a temperature not lower than said curing temperature of said thermosetting resin; inserting said powder rod in said mold; maintaining said powder rod as is, until said thermosetting resin is heated to about said softening temperature of said thermosetting resin by the heat from said pre-heated mold; inserting said piston in said mold so as to apply said second uniaxial pressure to said rod; and maintaining said rod at said second pressure to cure said thermosetting resin.

* * * * *